United States Patent [19]

Honneffer

[11] 4,198,964
[45] Apr. 22, 1980

[54] ACROMIOCLAVICULAR BRACE

[75] Inventor: Robert W. Honneffer, Warsaw, Ind.

[73] Assignee: Zimmer USA, Inc., Warsaw, Ind.

[21] Appl. No.: 2,672

[22] Filed: Jan. 11, 1979

[51] Int. Cl.² ............................................. A61F 5/04
[52] U.S. Cl. .................................. 128/87 R; 128/94; 128/DIG. 19
[58] Field of Search ............... 128/87 R, 94, DIG. 19, 128/83, 77

[56] References Cited

U.S. PATENT DOCUMENTS

| | | | |
|---|---|---|---|
| 2,460,589 | 2/1949 | Lewis | 128/94 |
| 3,404,680 | 10/1968 | Gutman et al. | 128/94 |
| 3,780,729 | 12/1973 | Garnett | 128/94 |

OTHER PUBLICATIONS

Orthopedic Clinics of North America, Apr., 1975 pp. 477-486.

Journal of Bone & Joint Surgery, Jan. 1952, pp. 232-233.
Orthopedic Clinics of North America, Jul. 1973, pp. 747-757.

*Primary Examiner*—John D. Yasko
*Attorney, Agent, or Firm*—Trexler, Wolters, Bushnell & Fosse, Ltd.

[57] ABSTRACT

A brace is provided for treatment of acromioclavicular dislocations. The brace includes a bandage member or body swathe which encircles the thorax and the involved upper arm, a resilient force focusing member or shoulder pad located atop the distal end of the clavicle, and reduction straps disposed between said members which operate through semblant pulleys to afford immobilization of the acromion and a multiplied reductive force on the dislocated clavicle whereby to hold the acromioclavicular joint in location.

7 Claims, 3 Drawing Figures

ACROMIOCLAVICULAR BRACE

BACKGROUND OF THE INVENTION

The present invention relates generally to treatment of the subluxation or dislocation of the distal end of the clavicle resulting from stretching or rupture of the acromioclavicular or coracoclavicular ligaments, and specifically to a support or brace for reducing an acromioclavicular dislocation by the immobilization and elevation of the acromion and depression of the distal clavicle.

The acromion, the outer end of the spine of the scapula, articulates with the clavicle to form the outer angle of the human shoulder. The main stability of this joint is provided by the superior acromioclavicular and coracoclavicular ligaments. Injury to the acromioclavicular joint may result in the stretching of these ligaments and of the synovial capsule, or the rupture of the capsule and the acromioclavicular ligament. Severe ligamentous injury involves the rupture of both the acromioclavicular and coracoclavicular ligaments. These injuries result in the elevation of the distal end of the clavicle.

While surgery may be indicated in severe disruptions of the acromioclavicular and coracoclavicular ligaments, rupture of the acromioclavicular ligaments or stretching of the synovial capsule or the acromioclavicular ligament are commonly treated by closed methods which allow the natural reparative process to take place. Of primary import in advancing this natural fibrous repair are (a) the elevation of the acromion, (b) the depression of the elevated clavicle toward the elevated acromion, and (c) constant immobilization of the joint to prevent further strain or disruption of the reparative process.

Commonly employed methods of closed treatment have included a claviculo-ulnar reduction harness for relocating the acromioclavicular joint and a forearm sling hung from the neck to provide immobilization and ninety degree flexion of the elbow. The Kenny-Howard sling, as known in the art, employs a forearm sling and reduction straps attaching the sling to a shoulder pad. These reduction straps, when tensioned, depress the distal end of the clavicle and exert an upward force on the acromion via the humerus to maintain reduction. In addition, a positioning strap exerts a medial force to maintain the position of the reduction straps and shoulder pad when the unrestrained arm moves away from the torso.

Other slings have included neck straps to hold the affected arm in ninety degree flexion. Also, straps have been devised which attach to the wrist and provide a tensioning force on the neck strap by encircling the buttock on the affected side.

However, the Kenny-Howard sling and other such devices are not without their disadvantages. The reduction force on the distal clavicle is limited to the tension produced on the claviculo-ulnar straps by the weight of the forearm applied directly to the shoulder pad through said straps.

Also, neck straps produce uncomfortable pressures on the patient's neck and potentially disruptive forces on the trapezius muscles which play a major role in the articulation of the acromioclavicular joint. Straps which encircle the buttock are uncomfortable and provide only marginal immobilizing forces in ambulatory patients.

In addition, while prior art devices often include a strap circumflexing the thorax which provides a medial force on the sling, the arm is still relatively free to move. Thus when the patient leans forward or walks, the slung arm moves forward relative to the torso presenting a risk of the destruction of the newly formed fibrous repair.

SUMMARY OF THE INVENTION

In accordance with the present invention, a body swathe or bandage member is provided to immobilize the acromioclavicular joint and elevate the acromion by encircling the involved upper arm and the thorax of the patient. The body swathe also serves as an anchoring site for reduction strap assemblies.

A force-focusing member or shoulder pad is further provided, positioned superior to the distal clavicle and beneath novel reduction strap assemblies, which course from the shoulder pad through force-multiplying pulley-like rings on the bandage member and strap assemblies and finally attached to an arm envelope disposed about the forearm portion of the affected limb.

It is thus an object of the invention to provide multiplied reduction force on a dislocated clavicle.

It is a further object of the invention to provide elevation of the acromion and immobilization of the acromioclavicular joint to promote undisrupted natural fibrous repair of acromioclavicular dislocations.

Various other objects, advantages and features of the present invention will be apparent from the following description, when taken in connection with the accompanying drawings, wherein the preferred embodiment of the invention is set forth for purposes of illustration.

DESCRIPTION OF THE PREFERRED EMBODIMENT

Figure 2:
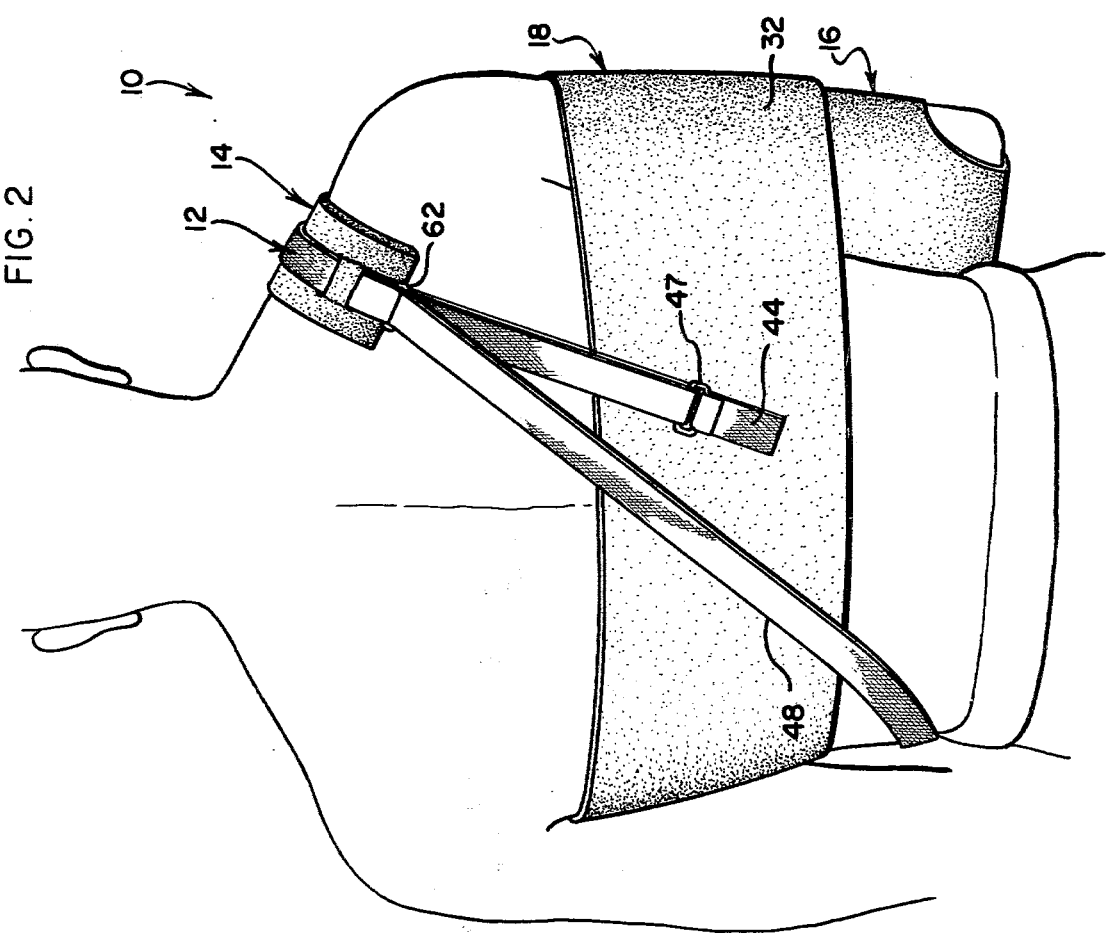
FIGS. 1 and 2 are respectively anterior and posterior views of a patient fitted with an acromioclavicular brace constructed in compliance with the present invention.
Figure 1:
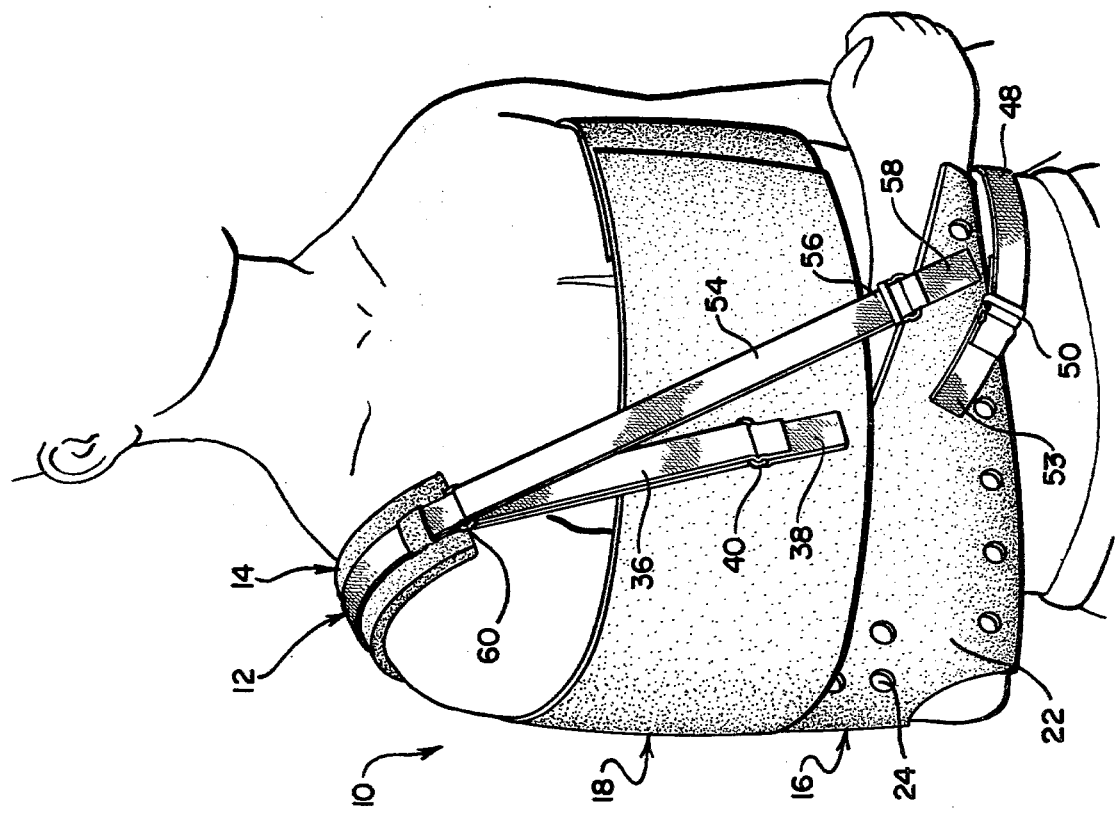

Referring to FIGS. 1 and 2, numeral 10 designates a preferred form of the invention. In this form there is a reduction strap assembly 12 desirably constructed of polyester webbing material, a shoulder pad 14 constructed of polyethylene foam, an arm envelope 16, and a body swathe 18 constructed of urethane foam-loop laminate material.

Figure 3:
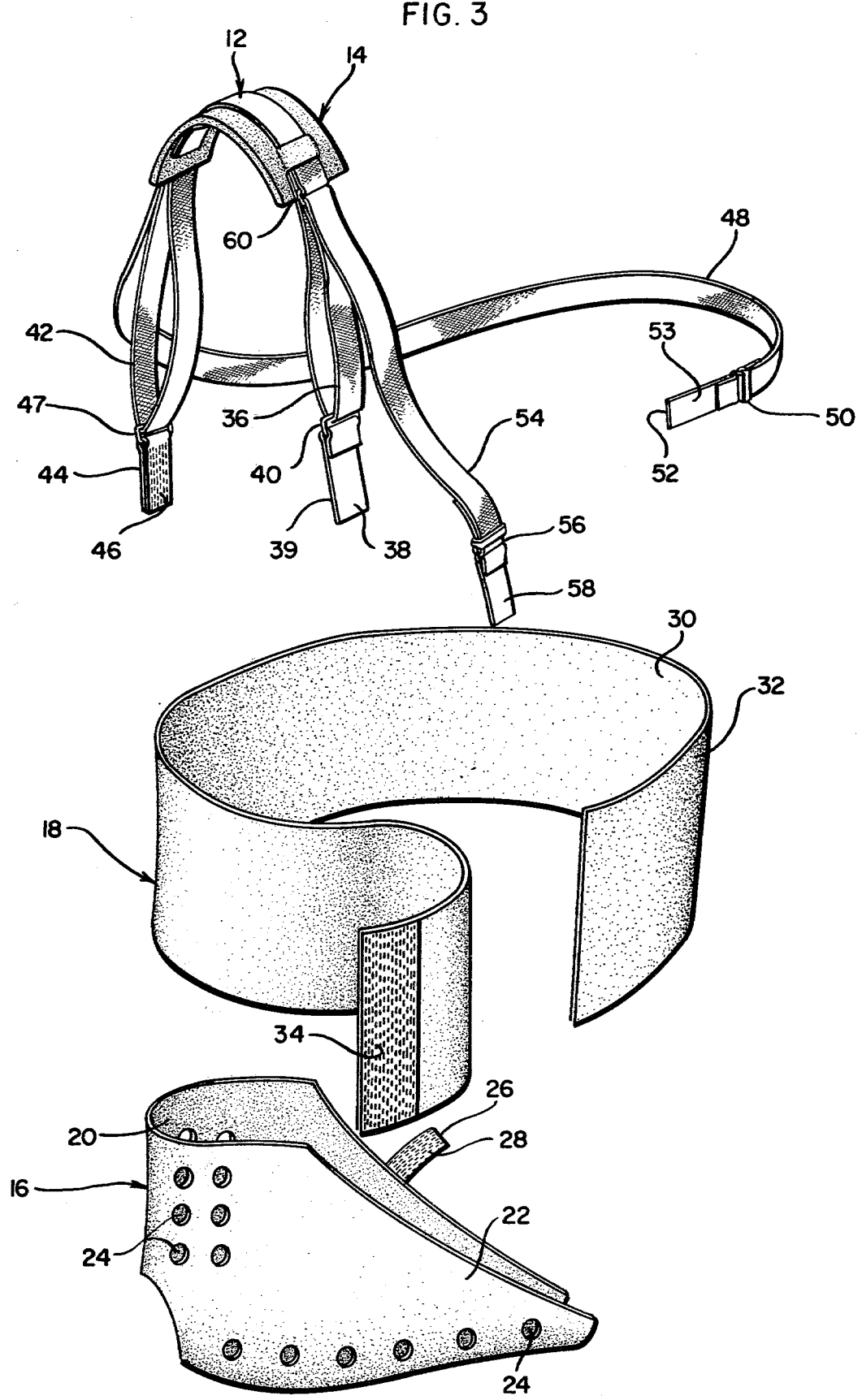
FIG. 3 is an anterior exploded view of the acromioclavicular brace of FIGS. 1 and 2 separately detailing the reduction strap assembly, body swathe and arm envelope member.

Turning to FIG. 3 for a more detailed description of arm envelope 18, that member is seen to include an inner layer of urethane foam 20 which is laminated to an outer layer of looped Velcro sensitive material 22 and perforated with a plurality of ventilation openings 24. Arm envelope 16 is applied over the lower portion of the arm on the same side as the acromioclavicular separation when the elbow is in flexion. The envelope 16 is closed by attaching tab 26 including hooked Velcro surface 28 to the looped Velcro sensitive material 22.

Also referring to FIG. 3, body swathe 18 is seen to have an inner layer of urethane foam 30 laminated to an outer layer of looped Velcro sensitive material 32 in addition to a Velcro hooked fastener surface 34 positioned at one end of swathe 18.

Returning to FIGS. 1 and 2, it will be noted that body swathe 18 is caused to encircle the patient's chest and upper arm on the affected side and then closed by attaching hooked fastener 34 to looped Velcro sensitive laminate 32 as shown in FIG. 3.

When body swathe 18 is thus secured, the affected acromioclavicular joint is immobilized and in proper position to receive the multiplied reduction force afforded by the novel reduction strap assembly 12 hereinafter described.

Shoulder pad 14 is then placed on the separated acromioclavicular joint so that front portion 36 of reduction strap assembly 12 lies across the patient's chest. Tab 38, including hooked Velcro surface 39, is then pressed against looped Velcro sensitive laminate 32 to fasten tab 38 and semblant pulley 40 to body swathe 18.

Turning to FIG. 2, rear portion 42 of reduction strap assembly 12 is positioned across the patient's back. Tab 44 including hooked Velcro surface 46, as shown in FIG. 3, is then pressed against looped Velcro sensitive laminate 32 to fasten tab 44 and semblant pulley 47 to body swathe 18.

As shown in FIGS. 1 and 2 rear strap 48 is then drawn around the patient's waist on the opposite side of the effected joint and terminal buckle assembly 50 is attached to Velcro sensitive laminate 22 of the front of arm envelope 16 using hooked Velcro laminate surface 52 on tab 53. The length of rear strap 48 may then be adjusted by terminal buckle assembly 50 to remove slack from rear portion 42 and rear strap 48 while shoulder pad 14 is maintained in position on the dislocated joint.

The dislocated clavicle is then reduced by placing downward pressure on the distal end of the clavicle through shoulder pad 14 along with upward pressure on the forearm. This force on the clavicle is maintained by sliding the hand down front strap 54 while simultaneously pulling downward. Terminal buckle assembly 56 is then adjusted to a suitable length and attached to Velcro sensitive laminate 22 of arm envelope 16 near the patient's wrist using hooked Velcro laminate 52.

As thus applied, the weight of the patient's arm provides a downward force which operates through movable semblant pully 60 and anchored semblant pulley 40, as shown in FIG. 3, to result in a multiplied reduction force being applied anteriorly to shoulder pad 14. This multiplied force is balanced by a similar force applied posteriorly by rear strap 48 through movable semblant pulley 62 and anchored semblant pulley 47. These multiplied forces are focused on the dislocated joint by shoulder pad 14 when terminal buckle assemblies 50 and 56 are adjusted to increase the tension on straps 48 and 54. These forces on arm envelope 16 bear against each other such that the tension on these straps may be increased while the arm is maintained in the desired position. In addition, the tension provided by rear strap 48 aids greatly in immobilizing the affected arm.

Although the invention has been described and illustrated with respect to a preferred embodiment thereof, it is to be understood that it is not to be so limited since changes and modifications may be made therein which are within the scope and spirit of the invention.

The invention is claimed as follows:

1. An acromioclavicular brace comprising: means attachable to the torso of an injured person for providing a first anchoring site for reduction strap assembly means and for providing an adductive force to the upper arm corresponding to an injured shoulder joint; mounting means for providing a second anchoring site for the reduction strap assemblies at a position disposed adjacent the ulna of the affected arm; a resilient force-focusing member adapted to be positioned superior to the distal end of the affected clavicle; semblant pulley means for providing mechanical advantage, said semblant pulley means including ring means having at least one straight, elongate portion; and at least one force multiplying reduction strap assembly means including two or more ambient pulley means and flexible connecting means adapted for coursing through said semblant pulley means and attaching to said first means mentioned, said second means mentioned, and said force focusing member whereby an adductive force is applied to said second named means and a multiplied reductive force is applied through the force focusing member to the affected distal clavicle.

2. An acromioclavicular brace comprising: means attachable to the torso of an injured person for providing a first anchoring site for reduction strap assembly means and for providing an adductive force to the upper arm corresponding to an injured shoulder joint; mounting means for providing a second anchoring site for the reduction strap assemblies at a position disposed adjacent the ulna of the affected arm; a resilient force-focusing member adapted to be positioned superior to the distal end of the affected clavicle; semblant pulley means for providing mechanical advantage, said semblant pulley means including a ring means having at least one straight, elongate portion; and reduction strap assembly means including a first semblant pulley means fixed ventrally to said first means mentioned, ventral strap means fixed to an anterior edge portion of said force-focusing member, said ventral strap means coursing inferiorly through said first semblant pulley means and returning superiorly through a second semblant pulley means fixed to an anterior edge portion of said force-focusing member and continuing inferiorly and attaching to the distal end of said second named means, whereby a multiplied reductive force affected by the weight of the involved arm is applied ventrally through the force-focusing member to the distal end of the affected clavicle, said reduction strap assembly means further including a first semblant pulley affixed dorsally to said first mentioned means, a second semblant pulley fixed to a posterior edge portion of said force-focusing member, dorsal strap means fixed to a posterior edge portion of said force-focusing means, said dorsal strap means coursing inferiorly through said first semblant pulley and returning superiorly through said second semblant pulley means and returning inferiorly and medially and continuing dorso-ventrally and attaching to said second named means, whereby an adductive force is applied to said second named means and a multiplied reductive force is applied through the force-focusing member to the distal end of the affected clavicle.

3. An acromioclavicular brace according to claim 1 or claim 2 wherein said first means mentioned further comprises a body swathe member encircling the chest and upper arm of a patient.

4. An acromioclavicular brace according to claim 1 or claim 2 wherein said mounting means further comprises an arm envelope adapted to enclose the lower arm of a patient.

5. An acromioclavicular brace according to claim 3 wherein said body swathe includes releasable attachment means.

6. An acromioclavicular brace according to claim 1 or claim 2 wherein said reduction strap assembly means is fixed to said first means mentioned by releasable attachment means.

7. An acromioclavicular brace according to claim 1 or claim 2 wherein said reduction strap assembly means is fixed to said first means mentioned by releasable attachment means.

* * * * *

UNITED STATES PATENT AND TRADEMARK OFFICE
CERTIFICATE OF CORRECTION

PATENT NO. : 4,198,964
DATED : April 22, 1980
INVENTOR(S) : Robert Honneffer

It is certified that error appears in the above-identified patent and that said Letters Patent are hereby corrected as shown below:

In the Abstract, line 5, after "," insert --an arm envelope member,--;

Column 3, line 43, change "movable" to --anchored--;

Column 3, line 44, change "pully" to --pulley--;

Column 3, line 44, change "anchored" to --moveable--;

Column 3, line 48, change "movable" to --anchored--;

Column 3, line 49, change "anchored" to --moveable--;

Column 4, line 10, change "ambient" to --semblant--.

Signed and Sealed this

Twelfth Day of August 1980

[SEAL]

Attest:

SIDNEY A. DIAMOND

Attesting Officer

Commissioner of Patents and Trademarks